United States Patent [19]

Spadafora et al.

[11] Patent Number: 5,491,157
[45] Date of Patent: Feb. 13, 1996

[54] METHOD AND COMPOSITION FOR THE PREVENTION, CONTROL AND AMELIORATION OF SOILBORNE FUNGI AND DISEASE CAUSED THEREBY

[75] Inventors: V. James Spadafora, Morrisville, Pa.; Thomas E. Brady, Hunterdon County, Readington Township, N.J.; Masatoshi Motoyoshi, Toyohashi, Japan

[73] Assignee: Eastman Kodak Company, Rochester, N.Y.

[21] Appl. No.: 59,690

[22] Filed: May 10, 1993

[51] Int. Cl.⁶ .................................................. A01N 43/78
[52] U.S. Cl. ............................ 514/369; 47/57.6; 504/100
[58] Field of Search ............................ 514/369; 548/184, 548/185

[56] References Cited

FOREIGN PATENT DOCUMENTS

| | | |
|---|---|---|
| 42-008799 | 12/1964 | Japan . |
| 45013814 | 10/1965 | Japan . |
| 44009312 | 10/1965 | Japan . |
| 44207723 | 11/1965 | Japan . |
| 42-008797 | 4/1967 | Japan . |
| 46039858 | 7/1969 | Japan . |
| 49-031096 | 8/1974 | Japan . |

OTHER PUBLICATIONS

K. Takatori, S. Asano, K. Nagata and A. Tao, (Gifu Coll. Pharm., Japan) Gifu Yakka Daigaku Kiyo No. 12, 27–33 (1962) [Chemical Abstract 58: 14635d] (Full Translation).
Chemical Abstract 54: 24666a [K. Takatori and S. Asano, (Gifu Coll. Pharm.) Yakugaku Zasshi 80, 789–80 (1960)].
Chemical Abstract 59: 11501F [Japan 18, 183(62)] (1963).
Chemical Abstract 59: 11518F [Japan 797(63)] (1963).
Chemical Abstract 56: 7328b [Japan 425(61)] (1960).
H. Wollmann, "Ueber den Einfluss antifungaler Substanzen auf den Säurestoffwechsel der Dermatophyten," Die Pharmazie 32(3):185–186 (Mar. 1977).
CA, vol. 82, No. 23, (1975), Abs. #150493v, Chiyomaru et al, "Fungicidal Composition for Agricultural Use," JP 74 31096.
CA, vol. 72, No. 21, (1970), Abs. #111461g, Takatori, Y. I., "2-(β–Chloro–Propionamido)-5-Thiocyanato Thiazole," JP 70 04,744.
CA, vol. 72, No. 9, (1970), Abs. #43653u, Takatori, Y II, "2-Form-Amido-5-Thiocyanato Thiazole," JP 69 30,269.

*Primary Examiner*—Glennon H. Hollrah
*Assistant Examiner*—Mary C. Cebulak
*Attorney, Agent, or Firm*—Peggy A. Climenson

[57] ABSTRACT

Methods and compositions utilizing 2-amino-5-thiazolyl thiocyanate compounds and their derivatives for the control of soilborne fungi and disease caused thereby are described.

18 Claims, No Drawings

METHOD AND COMPOSITION FOR THE PREVENTION, CONTROL AND AMELIORATION OF SOILBORNE FUNGI AND DISEASE CAUSED THEREBY

BACKGROUND OF THE INVENTION

Soilborne phytopathogenic fungi cause diseases which infest and infect growing and harvested crops and crop seed. Among the present methods used to combat the harmful effects of soilborne fungi are seed soak and seed drench practices. However, such practices have led to resistance problems, i.e., the target fungi develop resistant strains causing a loss of effectiveness of the fungicidal agent in use. Further, fungi such as Fusarium cause diseases which are difficult to control and result in significant reductions in yield and grain quality. Fusarium are also the sources of toxins produced in stored grains. Therefore, agriculturists continue to seek new, effective means of controlling soilborne phytopathogenic fungi and new compositions which would overcome resistance problems.

Simple aminothiazolylthiocyanates have been used for nearly a century as synthetic intermediates in heterocyclic chemistry and certain derivatives have been described as antibacterial agents, i.e., JP 74031096. However, there are no examples or teaching in the art of the use of 2-amino-5-thiazolyl thiocyanates and their derivatives for preventing, controlling or ameliorating soilborne phytopathogenic fungi. The use of 2-formamido-5-thiocyanatothiazoles and 2-acetamido-5-thiocyanatothiazoles for the control of medical pathogens such as Trichophyton and Candida and foliar pathogens such as *Piricularia oryzae* and *Alternaria solani* is described in Gifu Yakka Daigaku Kiyo, No. 12, 27–33(1962), (CA 58 14635d). However, the control, prevention or amelioration of soilborne pathogens by the use of 2-amido-5-thiocyanatothiazoles is not disclosed therein.

Therefore, it is an object of this invention to provide effective methods and compositions for the control, prevention or amelioration of soil fungal infestations utilizing 2-amino-5-thiazolyl ester thiocyanic acid compounds and derivatives thereof.

It is a further object of this invention to protect crops, both growing and harvested, from the damages caused by infestation and infection due to soilborne phytopathogenic fungi.

SUMMARY OF THE INVENTION

The present invention provides a method for the control, prevention or amelioration of soilborne phytopathogenic fungi which comprises contacting said fungi with a fungicidally effective amount of a compound of formula I

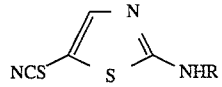

wherein R is hydrogen, $C_1$–$C_8$alkyl optionally substituted with one or more halogen or $C_1$–$C_4$alkoxy groups or $CXR_1$;

X is oxygen or sulfur and $R_1$ is hydrogen, $C_1$–$C_4$alkoxy optionally substituted with one or more halogens, $C_1$–$C_8$alkyl optionally substituted with one or more halogens, $C_1$–$C_4$alkoxy or phenyl optionally substituted with one to three halogen, $C_1$–$C_4$alkyl or $C_1$–$C_4$alkoxy groups or phenyl optionally substituted with one to three halogen, $C_1$–$C_4$alkyl or $C_1$–$C_4$alkoxy groups.

The present invention also provides a method to protect a crop plant or seed from attack by soilborne phytopathogenic fungi which comprises applying to the foliage of the plant or seed or to the soil or water in which the plant or seed is growing or about to be grown a fungicidally effective amount of a compound of formula I.

Further provided is a composition comprising an agronomically acceptable carrier and a fungicidally effective amount of a compound of formula I.

DESCRIPTION OF THE INVENTION

Many agronomic fungal diseases are not curable after detection and therefore pose a constant threat to growing and harvested crops. Soilborne fungi, such as Fusarium cause diseases which are difficult to control and which result in significant reductions in crop yield and grain quality. Fusarium fungi are also the sources of toxins such as zearalenones and trichothecines which are major problems in stored grains.

It has now been found that when used in the method of the invention, compounds of formula I provide effective control of troublesome and damaging soilborne phytopathogenic fungi such as Fusarium, Gaeumannomyces, Macrophomina, Sclerotinia and Thielaviopsos. These fungi are the causative agents of many of the major agronomic diseases such as wilt, root rot, stem rot, damping-off, seedling blight, foot rot, seed decay and the like. Among the important economic crops which may be protected by the inventive method are vegetable crops such as cucumber, tomato, cabbage, lettuce and the like; cereal crops such as wheat, rice, barley, corn, rye and the like and turf grass. In particular, the method of invention provides excellent control of severe soilborne diseases which are especially a problem in rice cultivation such as rice Bakanae disease, damping-off of rice and seed decay. Most particularly, the method of invention provides significantly high levels of control of Fusarium at exceptionally low rates of application.

Compounds useful in the method of invention are 2-amino-5-thiazolyl thiocyanate compounds of formula I

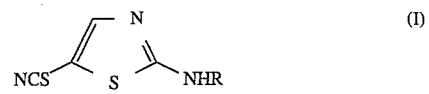

wherein R is hydrogen, $C_1$–$C_8$alkyl optionally substituted with one or more halogen or $C_1$–$C_4$ alkoxy groups or $CXR_1$;

X is oxygen or sulfur and $R_1$ is hydrogen, $C_1$–$C_4$alkoxy optionally substituted with one or more halogens, $C_1$–$C_8$ alkyl optionally substituted with one or more halogens, $C_1$–$C_4$alkoxy or phenyl optionally substituted with one to three halogen, $C_1$–$C_4$alkyl or $C_1$–$C_4$alkoxy groups or phenyl optionally substituted with one to three halogen, $C_1$–$C_4$alkyl or $C_1$–$C_4$alkoxy groups.

Compounds of formula I preferred for use in the inventive method are those wherein R is hydrogen or $COR_1$ and $R_1$ is $C_1$–$C_4$alkyl or phenyl optionally substituted with one to three halogen, $C_1$–$C_4$alkyl or $C_1$–$C_4$alkoxy groups. A compound of formula I more preferred for use in the inventive method is 2-amino-5-thiazolyl thiocyanate acid.

Compounds of formula I may be prepared by using commercially available 2-aminothiazole as starting material, alkylating or acylating the free amino group using standard alkylation or acylation procedures and then reacting the substituted-aminothiazole intermediate with bromine and potassium or ammonium thiocyanate to form the desired 2-(substituted)amino-5-thiazolyl thiocyanate acid compound of formula I. The reaction sequence is shown in flow diagram I wherein $R_2$ is $C_1$–$C_8$alkyl.

Flow Diagram I

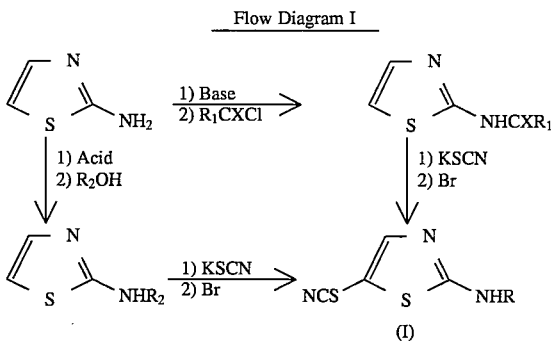

(I)

Alternatively, compounds of formula I may be prepared by first forming the 2-amino-5-thiazolyl thiocyanate acid by reacting 2-aminothiazole with potassium thiocyanate in the presence of bromine and then acylating or alkylating said thiocyanate.

Compounds of formula I, when used in accordance with the method of invention are effective for controlling, preventing or ameliorating the growth of soilborne phytopathogenic fungi in the presence of growing or harvested plants or plant seed. Although the compounds may be applied to the foliage or stems of the plant or to the plant seed or to the soil or water in which the plants or seed is growing or is to be grown, the preferred method of application is to the seed as a drench or soak to effectively defend the germinating seed from infection. Another preferred method of application is to the soil or water in which the plant or seed is growing or is about to be grown.

In actual agronomic practice, the compounds are applied to the soil or water in which the plant or seed is growing or is about to be grown in the form of a spray, powder, dust or granule, preferably as an aqueous spray. Generally, an aqueous solution or suspension containing about 20 ppm to about 1000 ppm, preferably 50 ppm–500 ppm of the formula I compound is suitable for use in the inventive method. Dust, powder or granular compositions which contain about 0.5% to about 95% weight/weight of the formula I compound may be used in the method of invention.

Compositions of the invention comprise a fungicidally effective amount of a compound of formula I and an agriculturally acceptable carrier. Compositions of the invention include liquid compositions such as aqueous solutions, aqueous suspensions, suspension concentrates, emulsifiable concentrates, concentrated microemulsions and the like and solid compositions such as wettable powders, dusts, dust concentrates, dry compacted granules and the like.

In accordance with the method of invention the 2-amino-5-thiazolyl thiocyanate compounds of formula I may be formulated or applied either alone or in combination with one or more pesticides or plant growth regulants. Pesticides used in combination may be herbicides, insecticides or other fungicides or a combination thereof. When the formula I compounds are applied in combination with another pesticide or pesticides, they may be applied simultaneously or sequentially. Among the available fungicides which may be used in combination with the formula I compounds are 4,6-dinitro-o-cresol, benalaxyl, benomyl, captafol, captan, carbendazim, chlorothalonil, copper, cymoxanil, dichlofluanid, dichlone, difenoconazole, dimethomorph, diniconazole, dinocap, dithianon, fenpiclonil, fenpropimorph, hymexazol, imazalil, iprodione, isoprothiolane, kasugamycin, mancozeb, mepronil, mercuric oxide, oxadixyl, oxolinic acid, penconazole, propineb, pyrifenox, thiabendazole, thiram, tolclofos-methyl, triadimefon, triflumizole, triforine, validamycin A, vinclozolin, zineb, ziram and the like.

For a more clear understanding of the invention, specific examples thereof are set forth below. These examples are merely illustrative and are not to be understood as limiting the scope and underlying principles of the invention in any way. The terms NMR, CIMS and IR designate nuclear magnetic resonance, chemical ionization mass spectrometry and infrared, respectively.

EXAMPLE 1

Preparation of 2-amino-5-thiazolyl thiocyanate

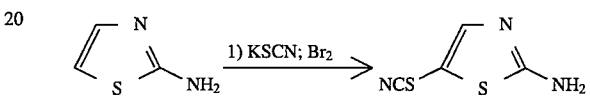

A stirred solution of 2-amino-5-thiazole (2.0 g, 20 mM) and potassium thiocyanate (3.80 g, 40 mM) in methanol is treated dropwise with bromine (3.2 g, 20 mM) at 10° C., allowed to warm to room temperature and poured over ice. The resultant reaction mixture is filtered to give the title product as a yellow solid (1.0 g, mp 142° C.), identified by $^1$HNMR, CIMS and IR analyses.

EXAMPLE 2

Preparation of 2-formamido-5-thiazolyl thiocyanate

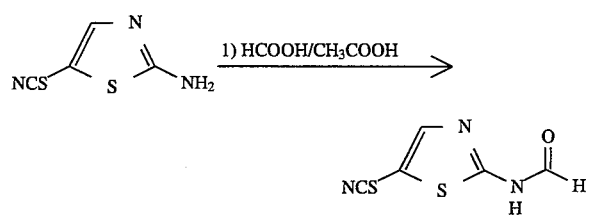

A mixture of 2.0 ml formic acid and 20 ml acetic anhydride is heated at reflux temperature for 2 hours, cooled in an ice bath, treated with 2-amino-5-thiazolyl thiocyanate (1.0 g, 6.37 mM), and stirred at ambient temperatures for 60 hours. The resultant reaction mixture is filtered to yield the title product as a yellow solid (0.65 g, mp 223°–225° C.), identified by $^1$HNMR, CIMS and IR analyses.

EXAMPLE 3

Preparation of 2-(isopropylamino)-5-thiazolyl thiocyanate

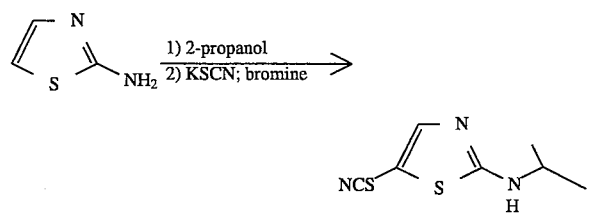

A solution of 2-aminothiazole (10.0 g, 100 mM) in 25 ml concentrated sulfuric acid is treated portionwise with 2-propanol (6.0 g, 100 mM), stirred at 50° C. for 2 hours, cooled and neutralized with 50% aqueous sodium hydroxide. The resultant reaction mixture is filtered to yield 2-(isopropylamino)-5-thiazole (13.0 g, mp 93°–94° C.).

A solution of the 2-(isopropylamino)-5-thiazole (2.82 g, 20 mM) and potassium thiocyanate (4.0 g, 40 mM) in methanol is treated dropwise with bromine (3.2 g, 20 mM) at 10° C., warmed to room temperature and concentrated in vacuo. The residue is triturated under water and filtered. The filtrate is treated with saturated aqueous sodium bicarbonate and the resultant precipitate is filtered off to yield the title product as a yellow solid (0.75 g, mp 184°–185° C.), identified by ¹HNMR, CIMS and IR analyses.

EXAMPLE 4

Preparation of 2-(t-butylamido)-5-thiazolyl thiocyanate

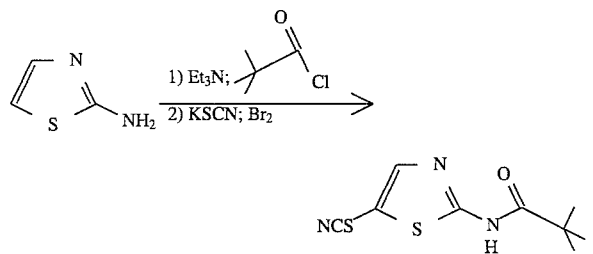

A solution of 2-aminothiazole (4.0 g, 40 mM) and triethylamine (4.04 g, 46 mM) is treated dropwise with pivaloyl chloride (40 mM) at room temperature, stirred for 1 hour, and filtered. The filtrate is evaporated to dryness to yield 2-(t-butylamido)-thiazole as a residue. The residue is dissolved in methanol, treated with 40 mM of potassium thiocyanate, and then treated dropwise with bromine (1.0 ml, 20 mM) at 10° C. The stirred reaction mixture is warmed to room temperature, poured over ice and filtered to give the title product as a yellow solid (2.06 g, mp 98°–100° C.), identified by ¹HNMR, CIMS and IR analyses.

EXAMPLES 5–9

Following essentially the same procedure described in Example 4 and using the appropriately substituted acid chloride, the following formula I compounds are obtained as shown in Table I.

TABLE I

| Example Nos. | $R_1$ | mp °C. |
|---|---|---|
| 5 | $CH_3$ | 152–154 |
| 6 | $OCH_2C_6H_5$ | 163–164 |
| 7 | $CH_2OCH_3$ | 119–121 |
| 8 | $OCH_3$ | 210–211 |
| 9 | $C_6H_5$ | 171–172 |

EXAMPLE 10

In Vitro Evaluation of Minimum Inhibitory Concentration Of Test Compounds

Target soilborne fungi are added to wells of 96-well plates as suspensions of propagules in a fungal growth medium. Test compounds are dissolved in dimethylsulfoxide, diluted with water in a 5× dilution series to appropriate concentrations then added to the 96-well plates containing the fungi. After fungal growth has occurred, the lowest concentration of each compound which inhibits 90% of fungal growth is recorded. Untreated control wells and wells treated only with the solvent (dimethyl sulfoxide) are used for comparison.

| Column Heading | Test Organisms Scientific Name |
|---|---|
| FUSAAV | *Fusarium avebaceum* |
| FUSACU | *Fusarium culmorum* |
| FUSAEQ | *Fusarium eguiseti* |
| FUSAGR | *Fursarium graminearum* |
| FUSACE | *Fusarium oxysporum* f.sp. *cepea* |
| FUSACC | *Fusarium oxysporum* f.sp. *cucumerinum* |
| FUSALY | *Fusarium oxysporum* f.sp. *lycorersici* |
| FUSAPO | *Fusarium poae* |
| FUSAPR | *Fusarium proliferatum* |
| FUSASI | *Fusarium solani* f.sp. *pisi* |
| FUSASG | *Fusarium subglutinans* |

Compounds are rated for the lowest concentration (measured in ppm) showing 90% or greater inhibition of fungal growth. (MIC90).

Compounds are also rated for the lowest concentration showing any inhibition of fungal growth.

The results are reported in Table II.

TABLE II

| | Minimum Inhibitory Concentration of Test Compounds (MIC90) | | | | | | | | |
|---|---|---|---|---|---|---|---|---|---|
| Test | (Concentration in ppm) | | | | | | | | |
| organism | Ex. 1 | Ex. 2 | Ex. 3 | Ex. 4 | Ex. 5 | Ex. 6 | Ex. 7 | Ex. 8 | Ex. 9 |
| FUSAAV | 5 | 25 | >125 | 25 | 25 | >125* | 5 | 25 | 25 |
| FUSACU | 5 | 25 | >125* | 25 | 25 | >125* | 25 | 25 | 5 |
| FUSAEQ | 1 | 5 | >125 | 5 | 5 | 25 | 5 | 5 | 5 |
| FUSAGR | 1 | 5 | >125 | 5 | 5 | 5 | 5 | 5 | 5 |
| FUSACE | 25 | 25 | >125 | 25 | 25 | >125* | 25 | 25 | 25 |
| FUSACC | 5 | 25 | >125 | 25 | 25 | >125* | 25 | 25 | 25 |
| FUSALY | 5 | 25 | >125 | 25 | 25 | >125* | 25 | 25 | 25 |
| FUSAPO | 5 | 25 | >125 | 25 | 25 | >125* | 5 | 25 | 25 |
| FUSAPR | 5 | 25 | >125 | 25 | 25 | >125* | 25 | 25 | 25 |
| FUSASI | 5 | 25 | >125 | 25 | 25 | >125* | 5 | 25 | 5 |
| FUSASG | 5 | 25 | >125 | 25 | 25 | >125* | 25 | 25 | 25 |

*Inhibition of fungal growth occurred but less than 90% at 125 ppm.

EXAMPLE 11

Evaluation of In Vitro Soilborne Fungicidal Activity of Test Compounds

Test compounds are dissolved in acetone and dispersed into cell well plates containing a suspension of ground fungal mycelia in a nutrient broth. Assay plates are incubated for 3–4 days at 21° C. Growth inhibition is measured visually and is rated using the following scale:

| Rating | % Inhibition |
|---|---|
| 0 | 0 |
| 1 | 1–29 |
| 3 | 30–59 |
| 5 | 60–89 |
| 7 | 90–99 |
| 9 | 100 |

Untreated controls, solvent blanks and reference standards are included in each test.

Assay fungi include the plant pathogens, *Fusarium Oxysporum* f.sp. *cucumerinum* (Fusoxc); *Pseudocercosporella herpotrichoides* (Psdche); *Pythium ultimum* (Pythul); *Rhizoctonia solani* (Rhizoc); Rice Bakanae Disease (RBD) and Cucumber Fusarium Wilt, *Fusarium oxysporum* f.sp. *cucumerinum* (CUFO).

The data obtained are shown in Table III.

TABLE III

Soilborne Fungicidal Evaluation of Test Compounds

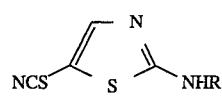

| R | FUSOXC (25 ppm) | PSDCHE (25 ppm) | PYTHUL (25 ppm) | RHIZOC (25 ppm) | RBD (125 ppm) | CUFO (1.25 kg/ha) |
|---|---|---|---|---|---|---|
| H | 9 | 9 | 9 | 9 | 7 | 8 |
| COCH$_3$ | 9 | 9 | 9 | 9 | — | — |
| CHO | 9 | 9 | 9 | 7 | — | — |
| COCH$_2$OCH$_3$ | 9 | 9 | 9 | 3 | — | — |
| COOCH$_3$ | 9 | 3 | 9 | 0 | — | — |
| COC(CH$_3$)$_3$ | 0 | 0 | 7 | 5 | — | — |

EXAMPLE 12

In Vivo Soilborne Fungicidal Evaluation of 2-Amino-5-thiazolyl Thiocyanate

Rice seeds are soaked in water for 3 days at 25° C. Germinated seeds are planted in plastic boxes (1/10 of nursery box) containing 400 ml of contaminated soil, and then the seeds are covered with 100 ml pasteurized soil and maintained in a moisture chamber (27° C., 100% relative humidity) for 3 days. Solutions of the test compound in a 5% acetone/water mixture containing 0.05% TWEEN® 20 are applied to each pot by drenching the soil surface with 50 ml of test solution prior to covering with pasteurized soil. Typical rates are 200 mg, 100 mg and 50 mg test compound per nursery box. Boxes are then moved to the greenhouse where they are subirrigated daily. Disease control evaluations are made 7–10 days after seeding by counting healthy seedlings and converting the data to a 0–9 scale, as follows. When more than 1 test is performed, the data are averaged. The results are shown in Table IV.

| Scale | % Disease Control |
|---|---|
| 0 | 0 |
| 1 | 1–14 |
| 2 | 15–29 |
| 3 | 30–44 |
| 4 | 45–59 |
| 5 | 60–74 |
| 6 | 75–89 |
| 7 | 90–95 |
| 8 | 96–99 |
| 9 | 100 |

| | Test Organisms |
|---|---|
| Column Heading | Scientific Name |
| F.r | *Fusarium roseum* |
| P.g | *Pythium graminicola* |
| R.s | *Rhizoctonia solani* |
| R.c | *Rhizopus chinensis* |
| G.v | *Gliocladium virens* |

TABLE IV

In Vivo Evaluation of 2-Amino-5-thiazolyl Thiocyanate

| Rate mg/N.Box* | F.r | P.g | R.s | R.c | G.v |
|---|---|---|---|---|---|
| 200 | 7.5 | 8.5 | 9.0 | 9.0 | 9.0 |
| 100 | 8.0 | 8.0 | 9.0 | 9.0 | 9.0 |
| 50 | 8.0 | 7.5 | 8.0 | 8.0 | 8.5 |

*mg of test compound per Nursery Box

EXAMPLE 13

In Vivo Soilborne Fungicidal Evaluation of 2-Amino-5-thiazolyl Thiocyanate

Rice Bakanae Disease (RBD)

Pathogen (*Fusarium moniliforme*) infected rice seeds (approximately 500=12 g) are soaked in 30 ml of solutions of test compounds in acetone/water mixtures containing 0.05% TWEEN® 20 in 6 cm diameter plastic cups for 24 hrs at 25° C. for disinfection. Typical concentrations of test compound used are 250, 500 and 1000 ppm. After 24 hrs, the test solutions are decanted from the cups and 30 ml of deionized water is added to the cups. The cups containing seeds are placed in 28° C. incubators for 2 days to initiate germination. Germinated seeds from each treatment are planted in two plastic boxes (1/10 size of nursery box) containing pasteurized potting medium and maintained in a moisture chamber for 3 days. Plants are then moved to the greenhouse where they are subirrigated daily. Disease control evaluations are made 3–4 weeks after seeding using the rating scale shown in Example 12. The results are shown in Table V.

Cucumber Fusarium Wilt Disease (CUFO)

Cucumber seeds (untreated) are germinated in a plastic box with high humidity at 25° C. for 2 days. Pasteurized soil (100 ml) is added to 6 cm plastic cups and covered with 30 ml of pathogen (*Fusarium oxysporum* f.sp. *cucumerinum*) contaminated soil. Cucumber seeds are planted on the contaminated soil and the seeds are covered with 20 ml pasteurized soil. Acetone/water solutions of test compounds are applied to each pot by drenching the soil surface with 15 ml of test solution. Treatments are then placed in a greenhouse for disease development. Disease control evaluations are made 14–18 days after treatment using the rating scale shown in Example 12. Results are shown in Table V.

TABLE V

In Vivo Evaluation of 2-Amino-5-thiazolyl Thiocyanate for Soilborne Fungal Control

| Rate (ppm) | Disease RBD | Rate (kg/Ha) | Disease CUFO |
|---|---|---|---|
| 1000 | 9 | 10.0 | 9 |
| 500 | 9 | 5.0 | 9 |
| 250 | 8 | 2.5 | 9 |

What is claimed is:

1. A method for the control or amelioration of soilborne phytopathogenic fungi which comprises directly contacting said fungi in the soil with a fungicidally effective amount of a compound of formula I

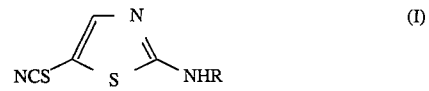

wherein R is hydrogen, CXR$_1$ or C$_1$–C$_8$ alkyl optionally substituted with one or more halogen or C$_1$–C$_4$ alkoxy groups;

X is oxygen or sulfur;

R$_1$ is hydrogen, C$_1$–C$_4$ alkoxy optionally substituted with one or more halogens, C$_1$–C$_8$alkyl optionally substituted with one or more halogens, C$_1$–C$_4$ alkoxy or phenyl optionally substituted substituted with one to three halogen, C$_1$–C$_4$ alkyl or C$_1$–C$_4$ alkoxy groups or phenyl optionally substituted with one to three halogen, halogen, C$_1$–C$_4$ alkyl or C$_1$–C$_4$ alkoxy groups.

2. The method according to claim 1 wherein the soilborne phytopathogenic fungi are selected from the group consisting of Fusarium, Gaeumannomyces, Macrophomina, Sclerotinia and Thielaviopsis.

3. The method according to claim 2 wherein the soilborne phytopathogenic fungi are Fusarium.

4. The method according to claim 3 wherein the Fusarium are *Fusarium oxysporum, Fusarium solani, Fusarium roseum* or *Fusarium moniliforme*.

5. The method according to claim 4 wherein the fungus is *Fusarium moniliforme*.

6. The method according to claim 1 having a formula I compound wherein R is hydrogen or COR$_1$ and R$_1$ is $C_1$–$C_4$alkyl or phenyl optionally substituted with one to three halogen, $C_1$–$C_4$alkyl or $C_1$–$C_4$alkoxy groups.

7. The method according to claim 6 having the formula I compound 2-amino-5-thiazolyl thiocyanate.

8. A method for protecting a plant or plant seed from attack by soilborne phytopathogenic fungi which comprises applying to the plant seed or the soil or water in which the plant or plant seed is growing or is to be grown a fungicidally effective amount of a compound of formula I

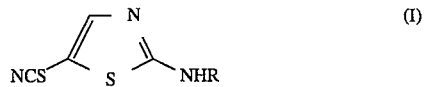

wherein R is hydrogen, $CXR_1$ or $C_1$–$C_8$alkyl optionally substituted with one or more halogen or $C_1$–$C_4$alkoxy groups;

X is oxygen or sulfur;

$R_1$ is hydrogen, $C_1$–$C_8$alkoxy optionally substituted with one or more halogens, $C_1$–$C_4$alkyl optionally substituted with one or more halogens, $C_1$–$C_4$alkoxy or phenyl optionally substituted with one to three halogen, $C_1$–$C_4$alkyl or $C_1$–$C_4$alkoxy groups or phenyl optionally substituted with one to three halogen, $C_1$–$C_4$alkyl or $C_1$–$C_4$alkoxy groups.

9. The method according to claim 8 wherein the formula I compound is applied to the plant seed.

10. The method according to claim 8 wherein the formula I compound is applied to the soil or water in which the plant or plant seed is growing or is to be grown.

11. The method according to claim 8 wherein the soilborne phytopathogenic fungi is selected from the group consisting of Fusarium, Gaeumannomyces, Macrophomina, Sclerotinia and Thielaviopsis.

12. The method according to claim 11 wherein the soilborne phytopathogenic fungi are Fusarium.

13. The method according to claim 12 wherein the Fusarium are *Fusarium oxysporum, Fusarium solani Fusarium roseum* or *Fusarium moniliforme*.

14. The method according to claim 13 wherein the fungus is *Fusarium moniliforme*.

15. The method according to claim 8 having the formula I compound wherein R is hydrogen or $COR_1$ and $R_1$ is $C_1$–$C_4$alkyl or phenyl optionally substituted with one to three halogen, $C_1$–$C_4$alkyl or $C_1$–$C_4$alkoxy groups.

16. The method according to claim 15 having the formula I compound 2-amino-5-thiazolyl thiocyanate.

17. The method according to claim 9 wherein the soilborne phytopathogenic fungi are Fusarium.

18. The method according to claim 10 wherein the soilborne phytopathogenic fungi are Fusarium.

* * * * *